(12) United States Patent
Augustine et al.

(10) Patent No.: US 7,120,951 B2
(45) Date of Patent: Oct. 17, 2006

(54) SYSTEM FOR WARMING LOWER EXTREMITIES OF SUPINE PERSONS

(75) Inventors: Scott Douglas Augustine, Bloomington, MN (US); Susan Dykins Augustine, Bloomington, MN (US); Garrett Jesse Augustine, Bloomington, MN (US); Brent Matthew Augustine, Bloomington, MN (US); Ryan Scott Augustine, Bloomington, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 129 days.

(21) Appl. No.: 10/198,842

(22) Filed: Jul. 19, 2002

(65) Prior Publication Data

US 2002/0178499 A1 Dec. 5, 2002

Related U.S. Application Data

(63) Continuation of application No. 09/439,548, filed on Nov. 12, 1999, now Pat. No. 6,473,920.

(51) Int. Cl.
*A47C 21/04* (2006.01)

(52) U.S. Cl. ............... 5/423; 5/421; 5/724; 5/941
(58) Field of Classification Search .......... 5/421, 5/423, 724, 726, 652.1, 941
See application file for complete search history.

(56) References Cited

U.S. PATENT DOCUMENTS

| | | | |
|---|---|---|---|
| 2,640,205 A | | 6/1953 | Simpson |
| 3,101,488 A | * | 8/1963 | Peebles .................. 5/423 |
| 3,230,556 A | * | 1/1966 | Shippee ................. 5/423 |
| 3,444,922 A | * | 5/1969 | Dingman ............... 165/247 |

(Continued)

FOREIGN PATENT DOCUMENTS

FR 851343 10/1960

OTHER PUBLICATIONS

Patent Abstracts of Japan: Publication No. 60053743, Publication date Mar. 27, 1985, Application Tottori Sanyo Electric Co Ltd.

(Continued)

*Primary Examiner*—Patricia Engle
*Assistant Examiner*—Fredrick Conley
(74) *Attorney, Agent, or Firm*—INCAPLAW; Terrance A. Meador

(57) ABSTRACT

A warming system, mounted to the foot of a bed, warms a person's lower extremities by directing air into the space between the mattress and overlaying blankets. A blower directs air into an elongated distribution chamber having many tiny exit apertures. The chamber is mounted at the foot of the bed, so that air exiting the apertures warms the person's feet. For maximum thermal transfer, the chamber is placed under the sheet and any blankets, but above the mattress cover and fitted sheet. The chamber may be implemented by a length of open cell foam, a hollow manifold with many punctures or other tiny distribution apertures, collapsible pocket, etc. While the person is lying on the bed beneath the blankets, with feet proximate the foot of the bed, the blower directs temperature-regulated air into the chamber and through the exit apertures, thereby warming the person's feet. A temperature regulator ensures a normothermic air temperature (or alternatively, hyperthermic air temperature.) Thus, the invention helps relieve or prevent "cold feet" by directing normothermic air at a person's lower extremities. Additionally, by applying heat to the feet and legs, the invention encourages blood flow by virtue of sympathetic vasodilation and local temperature-mediated vasodilation. The invention is also believed to prevent some leg and foot ulcers from forming by maintaining the lower extremity at a near normal temperature during sleep.

11 Claims, 6 Drawing Sheets

U.S. PATENT DOCUMENTS

| | | | | |
|---|---|---|---|---|
| 3,713,182 A | * | 1/1973 | McNeal | 5/421 |
| 3,778,851 A | * | 12/1973 | Howorth | 5/423 |
| 4,006,604 A | * | 2/1977 | Seff | 5/284 |
| 5,165,400 A | | 11/1992 | Berke | |
| 5,473,783 A | * | 12/1995 | Allen | 5/652.2 |
| 5,675,852 A | * | 10/1997 | Watkins | 5/638 |
| 5,887,304 A | * | 3/1999 | von der Heyde | 5/726 |
| 5,941,907 A | | 8/1999 | Augustine | |

OTHER PUBLICATIONS

Written Opinion from PCT/US00/41882.
International Search Report for PCT/US00/41822.
Written Opinion from PCT/US00/41882, dated Nov. 12, 2001.
Written Opinion from PCT/US00/41882, dated Jan. 22, 2002.

\* cited by examiner

SYSTEM FOR WARMING LOWER EXTREMITIES OF SUPINE PERSONS

This is a continuation of U.S. patent application Ser. No. 09/439,548, filed on 12 Nov. 1999, now U.S. Pat. No. 6,473,920.

BACKGROUND OF THE INVENTION

1. Field of the Invention

The present invention concerns external techniques to warm the human body for comfort, therapy, surgery, or other treatment. More particularly, the invention concerns a warm air blower that is mounted to the foot of a bed and utilized to direct warm air to the lower extremities of a supine person.

2. Description of the Related Art

Many people complain of having "cold feet" while laying in bed. For some people, they simply feel colder at any given temperature than other people. For others, the problem is more serious because they suffer from inadequate circulation to the legs and feet, resulting in abnormally cold feet and legs. In either case, the perception of cold feet can cause significant discomfort, especially while trying to sleep.

Normal body core temperature ("normothermia") occurs at about 37° Celsius. Body temperatures below this are considered "hypothermic," and have many negative physiological effects beyond mere discomfort. Temperature excursions of a mere 1–2° Celsius below normal can profoundly affect many cellular and physiological functions in areas such as the immune system, coagulation system, cardiovascular system, and death rates during surgery. According to one published study, surgical patients with a core temperature of 34–35° Celsius experienced three times more wound infections than persons maintained at 36° Celsius.

Historically, the definition of "normothermia" has been limited to the core thermal compartment of the body. The peripheral thermal compartment, including the legs and other extremities, is designed to act as buffer or insulator between the core and the environment. Therefore, the peripheral compartment is expected to be hypothermic under many circumstances. This is one example of an "evolutionary tradeoff." Namely, in order to maintain their core temperatures within a narrow range, warm blooded animals readily sacrifice warmness of the extremities.

This natural tendency toward peripheral hypothermia is exacerbated by vascular disease, which further reduces blood flow to the extremities. In fact, the combination of sacrificial hypothermia of the extremities and peripheral vascular disease can result in especially profound hypothermia of the legs. Persons with vascular insufficiency of the legs generally have colder legs, sometimes even approaching room temperature. These same persons are also prone to chronic non-healing skin wounds on their legs. These wounds may originate for various reasons, such as diabetes causing small vessel disease, external pressure causing local vascular occlusion, venous disease, and circulatory insufficiency reducing the blood flow and changing the hydrostatic gradients.

Whether peripheral hypothermia results from vascular disease, sacrificial hypothermia, or both, this condition inhibits important cellular functions of leg tissue. These cellular functions are not any different, or less important, than functions of cells in core vital organs. For example, a circulating immune cell does not know if it is fighting an infection in the heart or lungs, or the big toe. However, the extremities are more often hypothermic than the core vital organs, and therefore suffer more frequently from hypothermia-induced limitations.

Hypothermia in the lower extremities, then, is especially prevalent due to sacrificial hypothermia, peripheral vascular disease, or a combination of both. Peripheral hypothermia causes pain and possible interference with cellular functions of leg tissues.

SUMMARY OF THE INVENTION

Broadly, the present invention concerns a warming system, mounted to the foot of a bed, to warm a person's lower extremities by directing air into the space between the mattress and overlaying blankets. The system utilizes a blower to direct air into an elongated, air permeable, fluid distribution chamber. The chamber is mounted at the foot of the bed, and spans the bed from side to side so that air exiting the chamber warms the person's feet. For maximum thermal transfer, the chamber is placed beneath blankets and other layers that cover the person, but above any lower layers such as a mattress cover and fitted sheet. Various embodiments of the chamber are contemplated, such as a length of open cell foam, a hollow manifold that is naturally air permeable, air impermeable hollow manifold with many punctures or other tiny distribution apertures, collapsible tube, etc. While the person is lying in bed beneath the blankets, with feet proximate the foot of the bed, the blower directs temperature-regulated air into the chamber; when the air exits the chamber, it warms the person's feet. Temperature is regulated to provide an infusion of warmed air.

As discussed above, one embodiment of the invention may be implemented to provide an apparatus to manage temperature in a supine person's legs and feet. A different embodiment concerns a method to manage temperature in a person's lower extremities.

The invention affords its users with a number of distinct advantages. For example, the invention relieves or even prevents the discomfort of "cold feet" by directing normothermic air at a person's peripherally hypothermic lower extremities. Additionally, by applying heat to the legs, the invention encourages blood flow to the legs by virtue of sympathetic vasodilation and local temperature-mediated vasodilation. The invention is also believed to prevent some leg and foot ulcers from forming by maintaining the lower extremities at a near normal temperature during sleep.

Moreover, by warming the feet and legs during the sleep hours, the present invention is believed to help provide improved healing of chronic ulcers of the leg or foot that have resulted from vascular insufficiency of the legs. Recent experiments have shown promise for healing chronic wounds by warming them from a typically hypothermic state toward normothermia. Warming the wound toward a normothermic temperature helps enable normal cellular functions that are inhibited by hypothermia. As proposed by the present inventors, severely hypothermic wounds are believed to exist in a state of "suspended animation," where the cells are alive but inactive. Severe hypothermia causes cell division ("mitosis") to stop, enzyme and biochemical reactions to be slowed or stopped, cell membrane functions to be altered, and the immune system to be inhibited. The result is that wounds are slow to heal, if ever. Thus, by gently warming the peripheral extremities, the present invention contributes to the healing of chronic wounds that would otherwise linger due to hypothermic interference.

In contrast to other arrangements such as heating blankets, the invention focuses heated air primarily on persons' feet and lower legs. As the face and torso are sensitive to temperature, many people do not tolerate additional heat applied to the body during sleep. In fact, some people might turn a heating blanket off because they feel too warm, yet their legs and feet are still hypothermic. In contrast, people tolerate more heat applied to the legs than the body and face before complaining of feeling too warm. People with diabetes and vascular disease are even more heat tolerant, because they tend to lose sensation in their feet and legs. The present invention capitalizes upon these facts by focusing heat upon the lower extremities.

As another benefit, in the case of people with vascular disease, diabetes, or another condition causing poor circulation in the peripheral extremities, the invention preferably regulates the temperature of warming air to about 38° Celsius. This temperature is normothermic since it approximately coincides with the upper limit of the body's normal core temperature. The approach of this invention diverges from electric blankets and other known heating devices, which typically apply a hyperthermic temperature to a person in order to develop a temperature gradient. By using a normothermic temperature, the invention helps avoid thermal injuries such as burns, which can occur without a person's knowledge because of the reduced sensory perception in the peripheral extremities. By limiting the temperature of warming air to about 38° Celsius, the invention can still induce a sufficient temperature gradient to induce warming because a peripherally hypothermic person's feet and legs are colder than normal. While approximately 38° Celsius is the preferred air temperature, it should be noted that temperatures higher and lower than 38° Celsius are also contemplated. The invention also provides a number of other advantages and benefits, which should be apparent from the following description of the invention.

DETAILED DESCRIPTION

The nature, objectives, and advantages of the invention will become more apparent to those skilled in the art after considering the following detailed description in connection with the accompanying drawings.

HARDWARE COMPONENTS & INTERCONNECTIONS

Introduction

Figure 1:
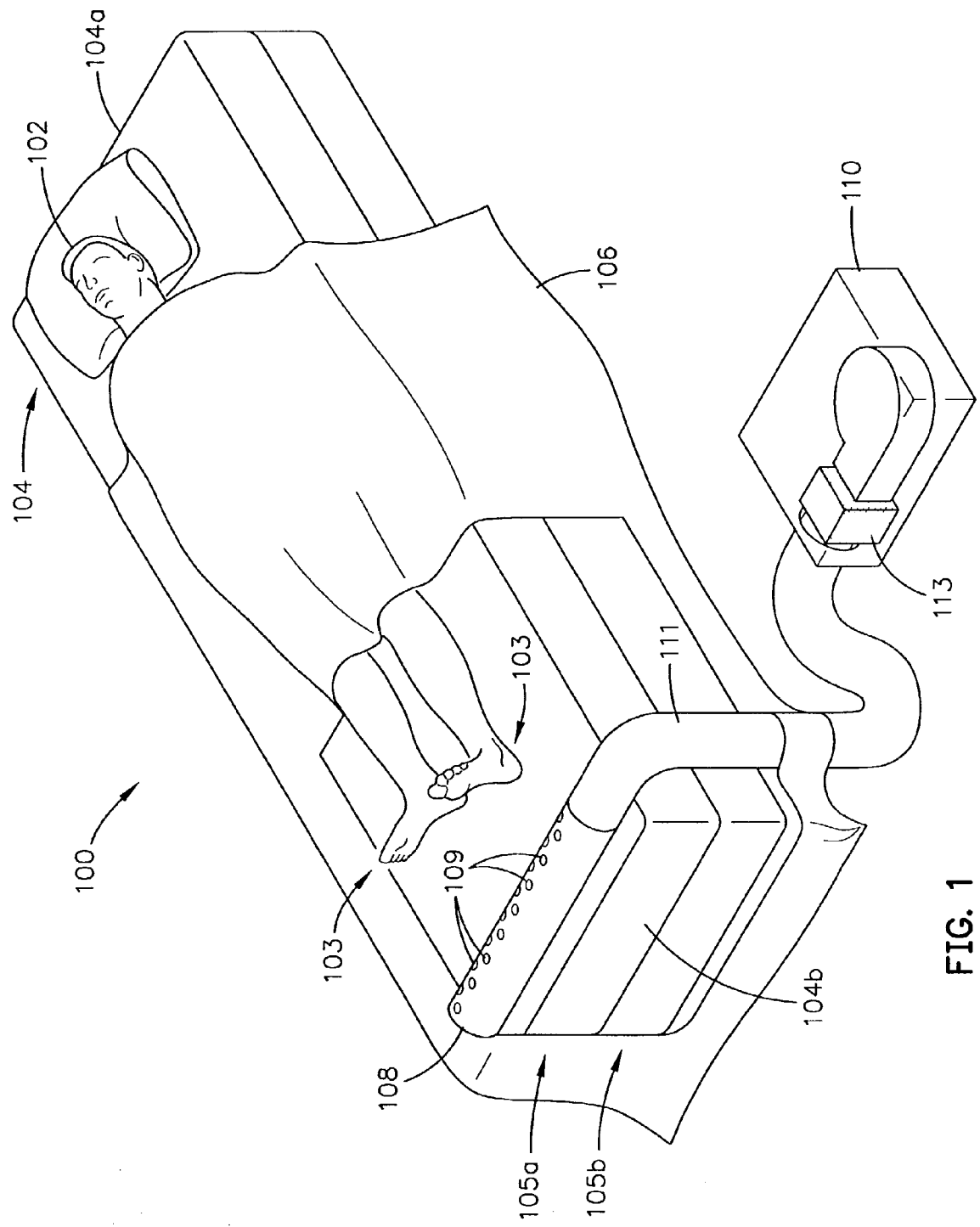
FIG. 1 is a perspective view of the hardware components and interconnections of one exemplary implementation of the invention.

As mentioned above, the invention concerns a warming system, mounted to the foot of a bed, to warm a person's lower extremities by directing air or another warm gas into the space between the mattress and overlaying blankets. Although many different hardware components and configurations may be used, FIG. 1 shows one example embodied by the system 100.

A person 102 is shown in supine position on a bed 104 that has a head end 104a and foot end 104b. The person is covered by one or more blankets 106. The system 100 employs a blower 110 to direct air into an elongated distribution chamber 108. The chamber 108 includes many tiny exit apertures 109. In one embodiment, the chamber 108 may comprise an otherwise air impermeable material, with many tiny apertures 109 defined therein. In another embodiment, the chamber 108 may comprise an air permeable substance such as a woven fabric, mesh, flexible lattice, fibrous structure, etc. The air permeable substance naturally defines many tiny apertures 109; additional apertures may be created to enhance air flow if desired.

The air is conditioned by a temperature regulator 113. The blower 110 and chamber 108 are coupled by a supply hose 111. The chamber 109 is mounted at the foot end 104b, so that air exiting the apertures 109 warms the person's feet 103. For maximum thermal transfer, the chamber 108 is placed under the blankets 106, but above any mattress cover, fitted sheet, and lower bedding. For ease of explanation, "upper sheet" is used to collectively refer to sheets, blankets, comforters, and other layers that cover the person. In contrast, "lower layers of bedding" refers to fitted sheets and other like materials that are placed about the mattress and therefore normally reside beneath a person in bed.

Bed

The invention may be implemented with nearly any sleeping arrangement. To provide some examples, the bed 104 may be a spring bed, air mattress, water bed, cot, hospital bed, cot, futon, or another sleeping surface. The mattress 105a may be supported by various structures, such as a box spring 105b (as illustrated), frame, floor, etc.

Air Distribution Chamber

Figure 2:
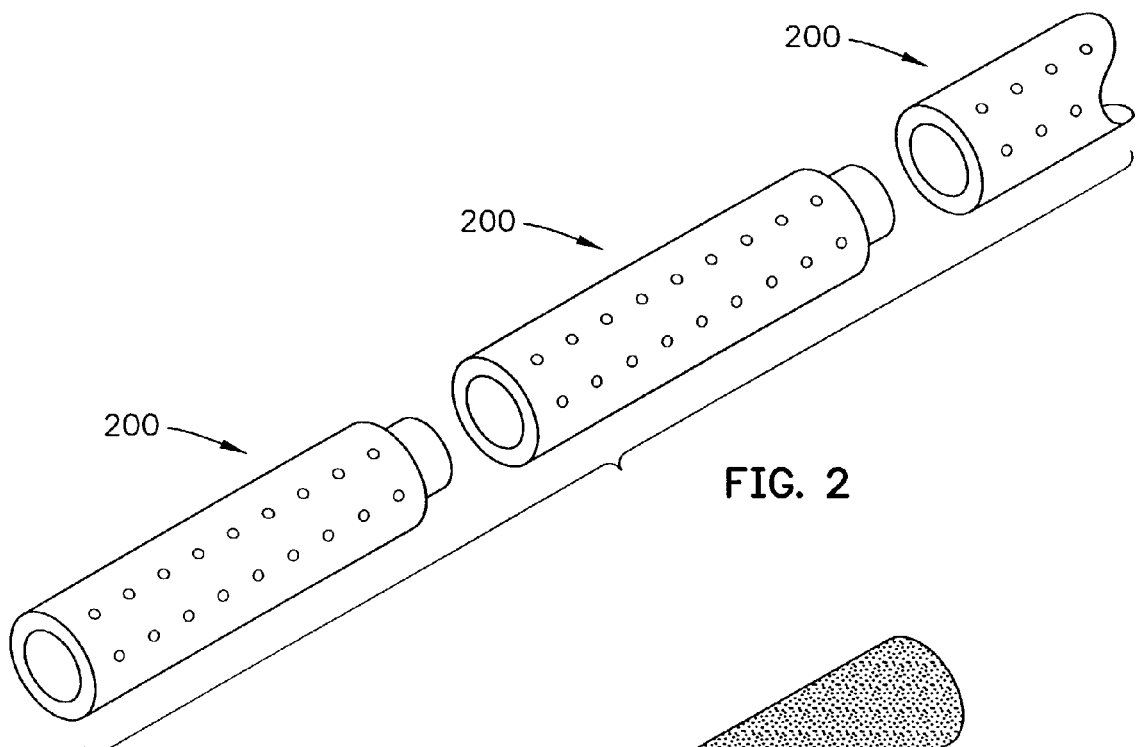
FIG. 2 is a perspective view of a adjustable length air distribution chamber according to the invention.
Figure 3:
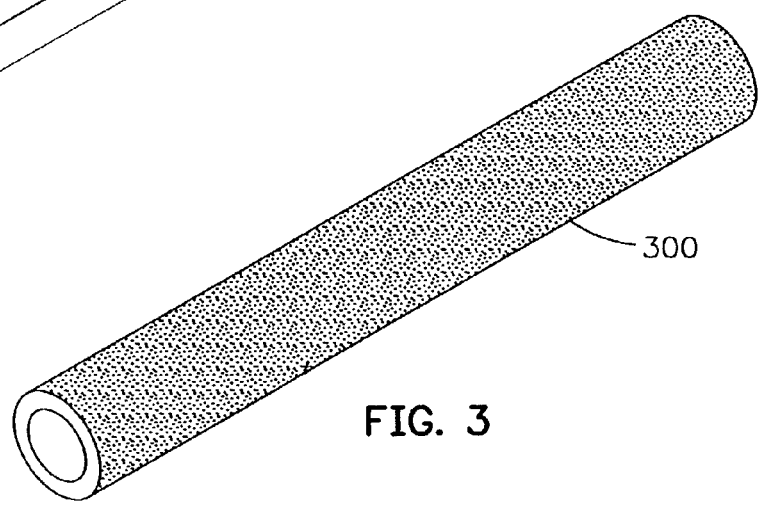
FIG. 3 is a perspective view of an inherently porous air distribution chamber according to the invention.

The chamber 108 extends across some or all of the bed's width, and may be constructed in various fashions. In the embodiment of FIG. 1, the chamber 108 includes a length of tubular conduit, such as semi-rigid plastic, defining many apertures 109 that allow air to escape. As shown in FIG. 2, the chamber may comprise sections 200 of conduit that snap screw, plug, slide or otherwise join, permitting the user to adjust the conduit's overall length according to the bed size. In a different example (FIG. 3), the chamber 108 comprises an air permeable material such as a length 300 of open cell foam, sponge, fibrous material, mesh, etc. The apertures in the chamber may be the natural spaces within the porous material, and/or additional channels, pores, or other openings may be created.

Figure 4:
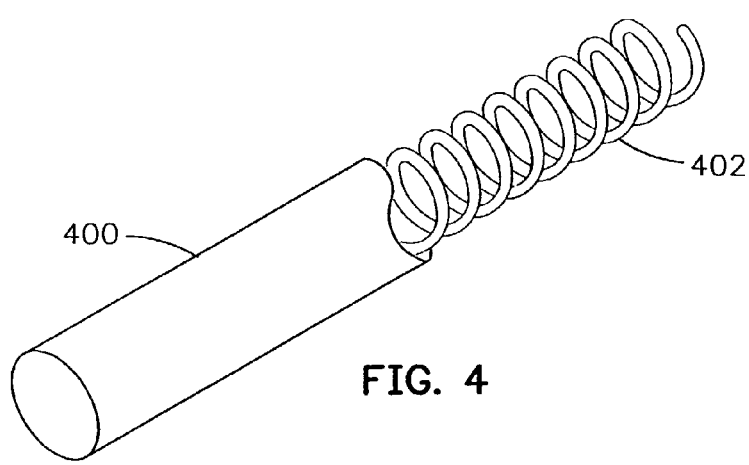
FIG. 4 is a perspective, partially cutaway view of a collapsible air distribution chamber with a helical support structure according to the invention.

In still another embodiment (FIG. 4), the chamber 108 may comprise a collapsible pocket 400 that inflates whenever it receives air from the blower 110. This collapsible structure may comprise cloth, plastic, or another suitably pliable material. The pocket 400 may optionally include a semi-rigid helix 402, lattice, or other internal supporting structure to maintain the chamber 108 in tubular form. The collapsible structure may include natural air permeability and/or apertures defined therein.

Mounting Hardware

During use, the air distribution chamber 108 is placed at the foot of the bed 104. The chamber 108 may be used with or without being mounted. In most cases, however, the chamber 108 preferably secured by some mounting hardware, which is described as follows. The chamber may be positioned in many ways, with a suitably diverse selection of mounting hardware. The chamber may be located between the blankets and the lower layers of bedding, or it may be integral with the mattress, blanket or lower layers of bedding.

Figure 5:
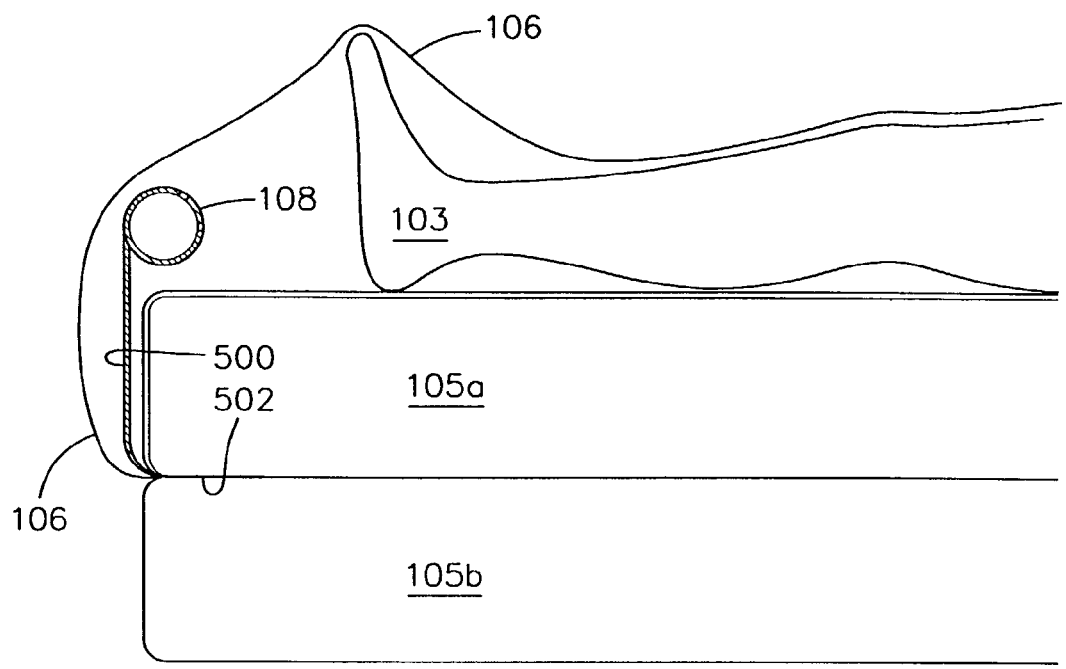
FIGS. 5–10 are cross-sectional side views showing various embodiments of mounting hardware to position the air distribution chamber according to the invention.

FIG. 5 shows one embodiment of mounting hardware, which utilizes a first member 500 of flat, relatively rigid material, such as a plastic sheet or bar. This member 500 is positioned between the vertical side of the foot end of the mattress and the blankets 106. The blankets 106 are tucked under the mattress 105a and wrap around the first member 500 and chamber 108, and then cover the person. This embodiment of mounting hardware also includes a second member 502 of flat, relatively rigid material, sandwiched between the bottom side of the foot end of the mattress 105a and the box springs 105b (or other structure beneath the mattress). As shown, the second member 502 is attached to the first member at substantially ninety degree angle, and helps secure the first member 500 and chamber 108 in position.

Figure 6:
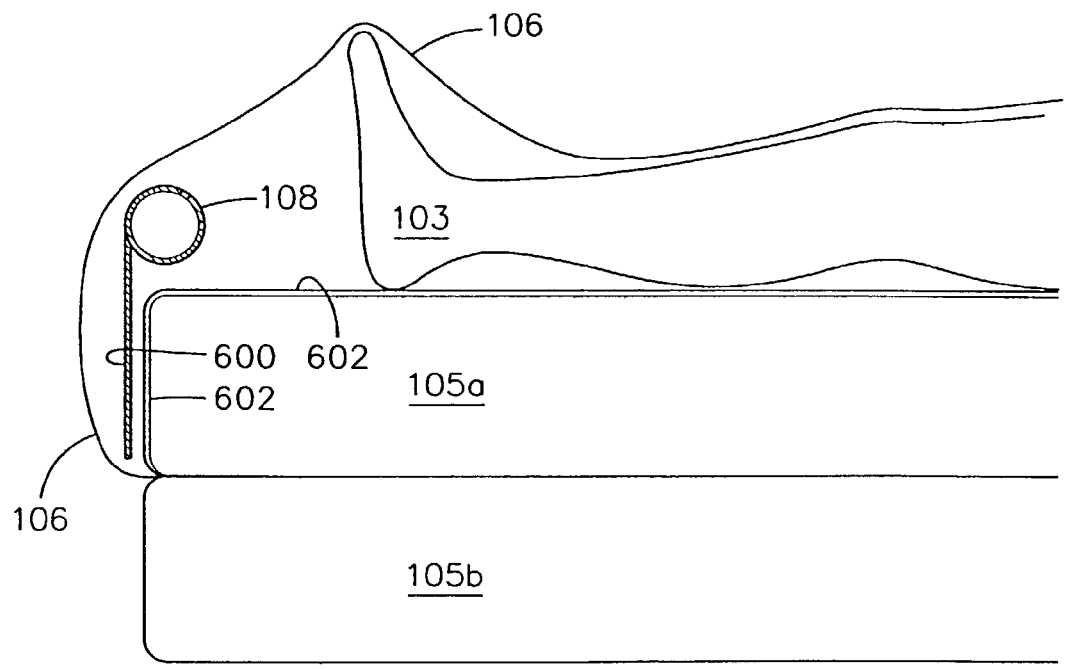

FIG. 6 shows a different embodiment of mounting hardware, which positions the chamber 108 using a first member 600 only. The second member 502 (FIG. 5) is omitted. The first member 600 is held in place by the blankets 106, which are firmly tucked in between the mattress 105a and box spring 105b. Alternatively, the first member 600 may be held in place by other means, such as (1) slidable insertion into a vertical pocket sewn into the lower layer of bedding 602 at the foot of the bed, (2) slidable insertion into a vertical pocket sewn into the lowermost layer of blanket 106, or (3) fasteners attaching the member 600 to the sheet or blankets. Some exemplary fasteners include hook and loop (e.g., VELCRO brand), snaps, clips, adhesive, etc.

Figure 7:
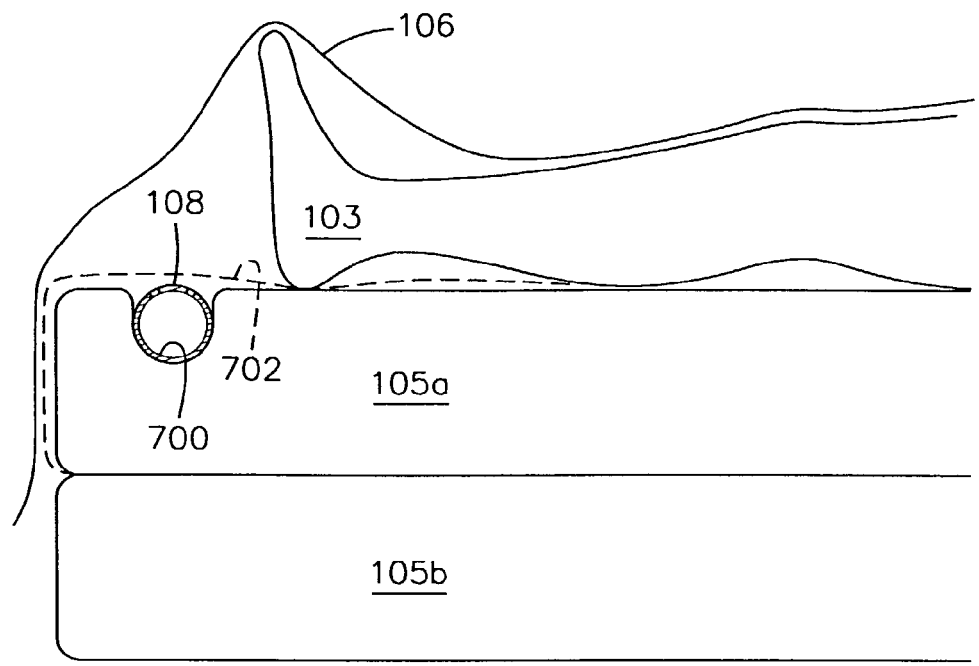

FIG. 7 shows a different embodiment of mounting hardware. In this arrangement, the chamber 108 resides in a channel 700 defined in the mattress 105a. The chamber 108 is held in place by the walls of the channel 700. Additionally, the chamber 108 may be positioned beneath a lower layer of bedding 702, further holding the chamber 108 in the channel 700.

Figure 8:
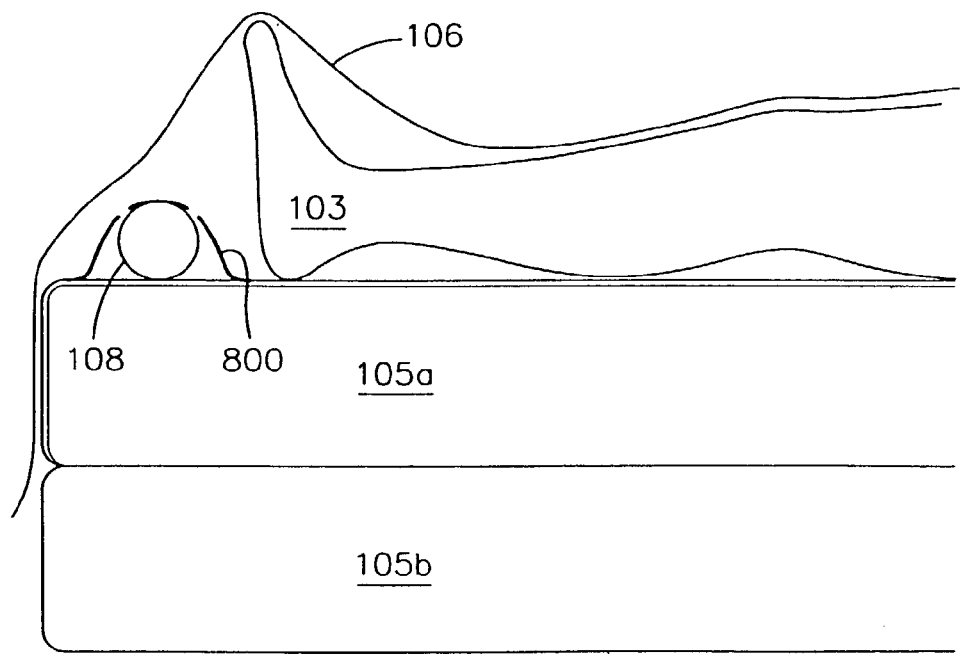

FIG. 8 shows a different embodiment of mounting hardware. In this setup, the mattress 105a does not include a channel 700 (as in FIG. 7), but the chamber 108 is nonetheless held in position by virtue of being placed beneath the lower layer of bedding 800. The chamber 108 may be further fixed in position by sewing the chamber 108 into the lower layer of bedding 800, or a pocket sewed thereto. Alternatively, instead of using the lower layer of bedding 800, the chamber 108 may be fixed in position by sewing the chamber into a layer of the blanket 106, or a pocket sewed thereto.

Figure 9:
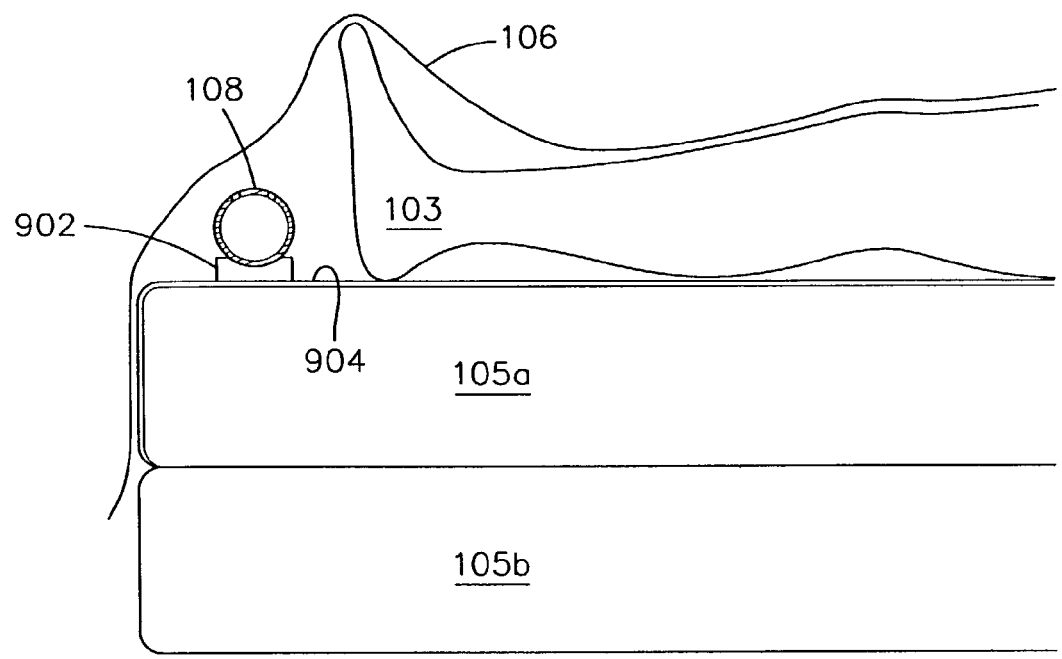

FIG. 9 shows still another embodiment of mounting hardware. In this arrangement, the chamber 108 is secured to a support structure 902 that is secured to a lower layer of bedding 904. The support structure 902 serves to keep the chamber 108 fixed in position, keep the chamber's apertures (e.g., apertures 109 in FIG. 1) oriented correctly to blow air toward the patient's feet 103, and keep the chamber 108 properly aligned with the bed. The support structure 902 may be implemented in many different ways, such as a molded plastic construction shaped to receive the chamber 108 and attached to the bedding 904 by hook and loop fasteners, fabric straps, adhesive strips, etc. Such a molded plastic construction may run along some or all of the chamber's length, and may even be implemented by several small brackets located at various points along the chamber's length.

Figure 10:
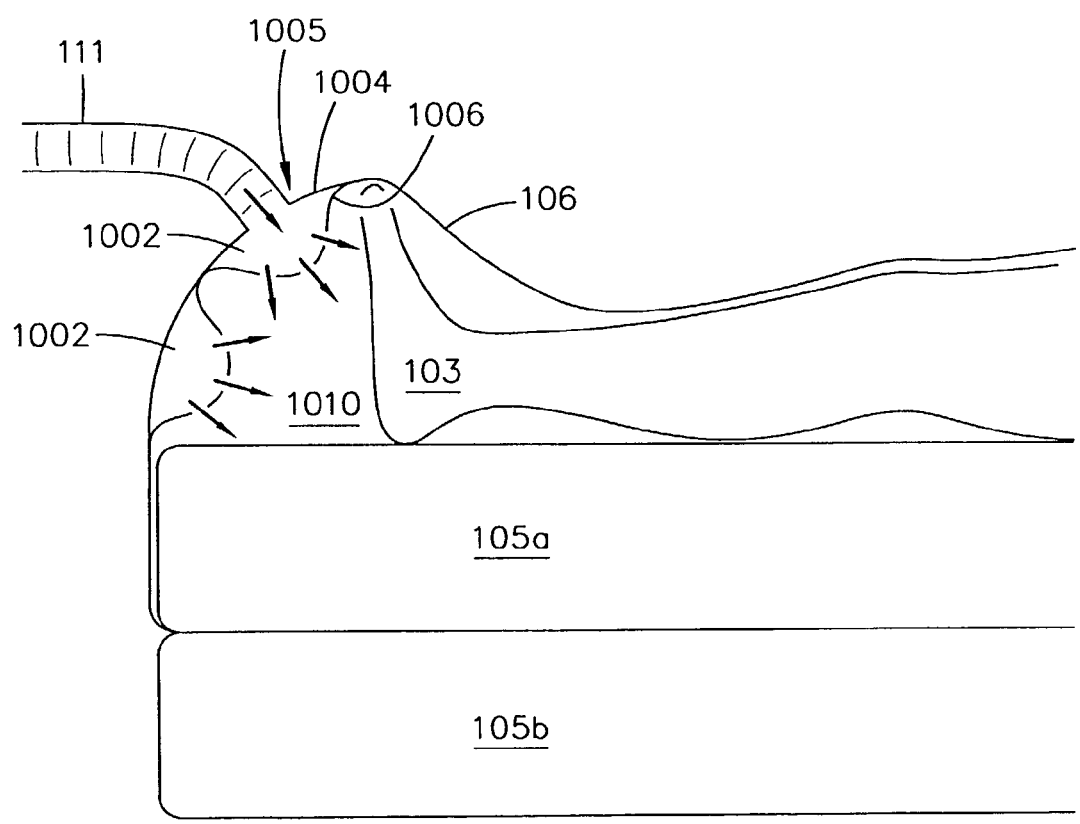

FIG. 10 shows a different embodiment of mounting hardware. In this arrangement, there exists a specially configured structure toward the foot of the bed. This structure includes an air impermeable outer layer 1004 and an air permeable inner layer 1006. The outer layer 1004 has an inlet 1005, permitting air from the supply hose 111 to enter the spaces between the layers 1004, 1006 and inflate one or more air channels 1002. FIG. 10 shows two such inflatable channels 1002 in cross-sectional view. If desired, the channels 1002 may be collapsible whenever air does not flow from the supply hose 111. Optionally, each channel 1002 may include an internal support member such as a helix of plastic or wire.

Since the inner layer 1006 is air permeable, air from the channel 1002 is exhausted through the layer 1006 into the space 1010 around the patient's feet 103. In one embodiment, the inner layer 1006 may comprise an otherwise air impermeable material with air exit apertures therein. In another embodiment, the inner layer 1006 may comprise an air permeable material, such as a woven fabric, mesh, flexible lattice, fibrous structure, etc.

The layers 1004, 1006 may be sewn, attached, or otherwise incorporated into the blankets 106. Alternatively, the layers 1004, 1006 themselves may provide a lower-body blanket that lies beneath the blankets 106 or between blanket layers, with or without connection to the blankets 106.

Blower

As mentioned above, one component of the system 100 is a blower 110 (FIG. 1). The blower 110 forces air into the air distribution chamber 108 via the supply hose 111. Under pressure from the blower 110, air passes through the apertures 109 and exits the chamber 108 into the space where the person's feet 103 reside between the blankets 106 and bed 104. Air from the chamber 108 remains trapped in a space created by the person's feet between the mattress and the blankets, and thereby warms the person's feet during a period of extended contact.

When used with sensitive surgical or other hospital patients, the blower 110 should comprise a quiet unit. In an exemplary application, the blower may provide an output air flow between five and twenty-five cubic feet per minute. However, the airflow may vary widely from this range depending upon the specific design of the chamber 108, apertures 109, hose 111, etc.

For ease of illustration, the present description depicts a blower 110 that withdraws air from the atmosphere and blows this air into the hose 111. In certain applications, however, ambient air may be undesirable for health, hygiene, therapy, or other reasons. Under these circumstances, the blower 110 may withdraw air from a prescribed vessel, filter, or other non-ambient air source. Thus, the blower 110 may be operated to provide filtered air, a substance other than air, or a greater concentration of a gas normally present in air (e.g., oxygen), etc. Additionally, the blower 110 may mix different input gases, such as injecting medication into the blower's air stream, or even mixing two non-air substances. Furthermore, in some cases, non-gas fluids may be utilized in small amounts, e.g. adding water vapor to increase humidity, etc.

Temperature Regulator

As mentioned above, the system 100 also includes a temperature regulator 113. The regulator 113 may be integrated into the blower 110, or it may be separate. In an integrated embodiment, the blower/regulator may comprise a self-contained unit such as a space heater. Whether integrated with the blower 110 or not, the temperature regulator 113 may be configured to condition air before, during, or after the air is moved by the blower 110. As one example, the regulator 113 may comprise an electrical resistance type heater.

The temperature regulator 113 may be implemented in many different ways. As one example, the regulator may comprise a digital data processing apparatus that operates by executing a sequence of machine-readable instructions. Examples of this embodiment include microprocessors, personal computers, computer workstations, and the like. One embodiment of regulator that is suitable for this implementation uses time-based temperature regulation. For example, the regulator 113 may be programmable to decrease or increase the air temperature after a selected period of time, turn the unit "on" or "off" at prescribed times, etc.

A different embodiment of the regulator 113 uses logic circuitry instead of computer-executed instructions to perform similar temperature control functions. Depending upon the particular requirements of the application in the areas of speed, expense, tooling costs, and the like, this logic may be implemented by constructing an application-specific integrated circuit (ASIC) having thousands of tiny integrated transistors. Such an ASIC may be implemented with CMOS, TTL, VLSI, or another suitable construction. Other alternatives include a digital signal processing chip (DSP), field programmable gate array (FPGA), programmable logic array (PLA), and the like. The regulator 113 may even use discrete circuitry, such as resistors, capacitors, diodes, inductors, transistors, and other components configured as a feedback loop or other circuit structure to automatically control temperature.

One specific example of the temperature controller 113 employs an electronic or electro mechanical temperature controller. For instance, the temperature controller may sense output air temperature and adjust the electrical current provided to the heater element to maintain an operator-specified output air temperature. As a different example, the regulator 113 may employ multiple heating elements that can be independently activated. For lower temperatures, a single element may be energized whereas for higher temperatures, multiple elements may be energized. In this case, the regulator 113 selectively activates the multiple heater elements using predetermined information such as a lookup table correlating various combinations of activated heater elements with empirically determined output temperatures likely to be produced under average room temperature conditions.

Depending upon the particular hardware used to construct the regulator 113, an operator may use various means to select the desired temperature. For instance, an operator may select the desired temperature by programming the regulator 113 (which subsequently operates automatically), turning a dial, punching a keypad, adjusting a rheostat, sliding a lever, etc.

The temperature of the blower's output air is important for various reasons. As mentioned above, the present inventors recognize that persons with diabetes and other vascular diseases frequently lose sensation in their feet and legs. These people are prone to foot injuries because they cannot feel blisters and other injuries forming, and therefore fail to take any preventive action. Relatedly, these people are prone to burn injuries because they cannot feel the temperature and pain of thermal damage to the skin. Thermal damage to inadequately perfused skin can occur at temperatures as low as 40° Celsius. By most standards, 40° Celsius is merely warm, not hot, yet in the case of inadequate blood flow to the skin, this temperature can cause a thermal injury or burn. Therefore, for the foregoing reasons, it may be desirable for the temperature regulator 113 to warm the air around the person's feet to a temperature that is greater than room temperature and less than 40° Celsius. As a more specific example, the regulator 113 may warm air to a temperature corresponding the upper limit of normothermia, such as about 38° Celsius. Limiting air temperature to the upper limit of normothermia is especially desirable to avoid skin damage in people that have limited sensation in their lower extremities due to diabetes, vascular disease, or another condition affecting circulation.

OPERATION

Figure 11:
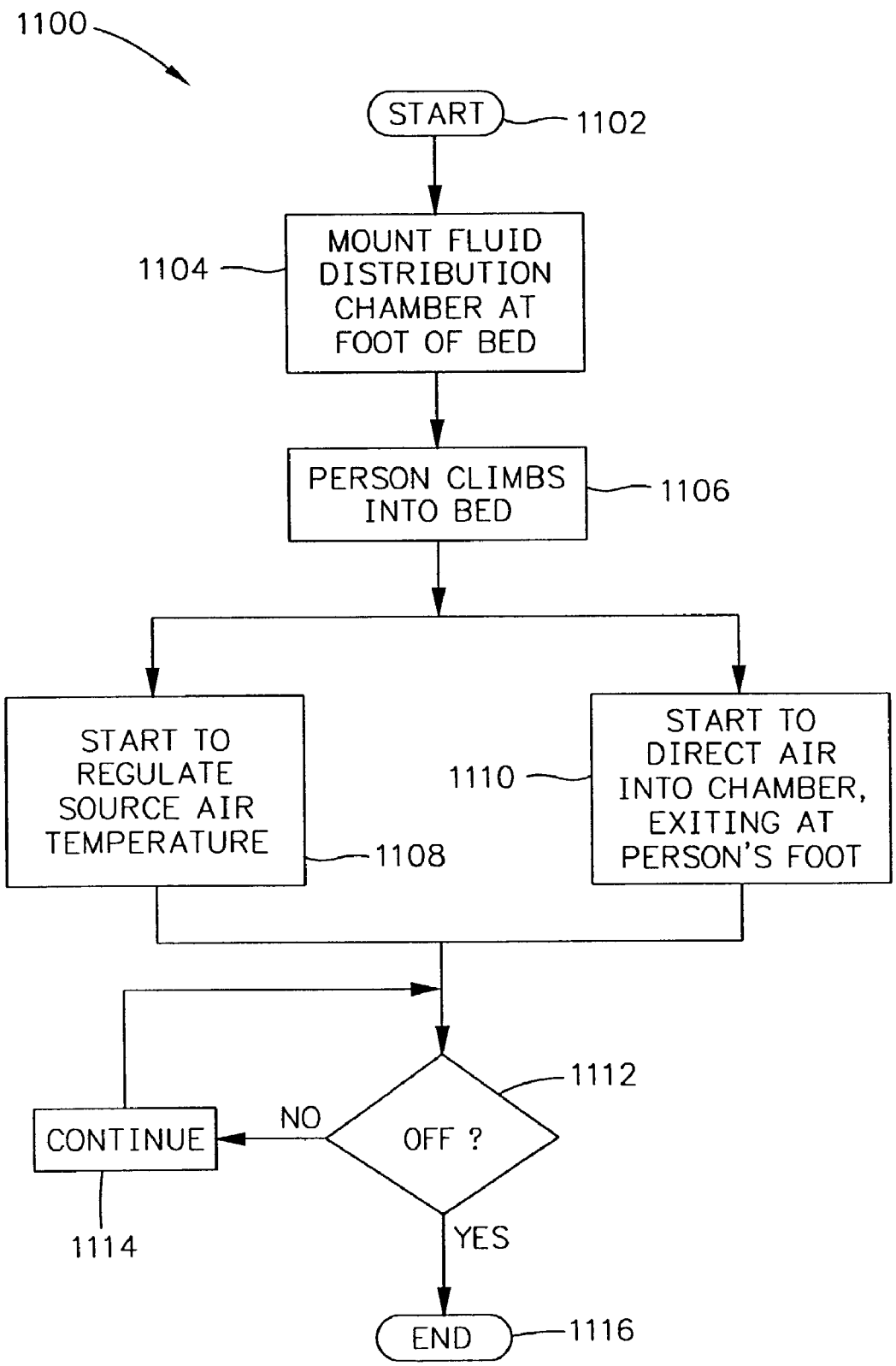
FIG. 11 is a flowchart of an operational sequence for warming the lower extremities of a supine person according to the invention.

In addition to the various hardware embodiments described above, a different aspect of the invention concerns a method to manage temperature in a person's lower extremities. FIG. 11 shows a sequence 1100 to illustrate one example of this aspect of the invention. For ease of explanation, but without any intended limitation, the example of FIG. 11 is described in the context of the system 100 described above.

The steps 1100 are initiated in step 1102. In step 1104, medical staff use mounting hardware as described above to affix the air distribution chamber 108 at the foot of the bed 104. If desired, the chamber 108 may be laid at the foot of the bed without any attachment. Step 1104 also includes the additional steps of attaching the hose 111 to the chamber 108 and blower 110, applying electrical power to the blower 110, selecting the desired output temperature, entering any additional programming the blower 110 if applicable, etc. In step 1106, the person 102 gets into bed. If desired, the order of steps 1104, 1106 may be reversed or even combined.

After step 1106, with the person 102 and the warming system in place, steps 1108, 1110 are performed. In step 1108, the temperature regulator 113 begins to regulate the temperature of the air or other air being supplied by the blower 110. As discussed above, the regulator 113 provides output air temperature near the upper limit of normothermia, or about 37° Celsius. For people with normal pain sensation in the feet, the regulator 113 may even produce hyperthermic temperatures. Concurrently with step 1108, the blower 110 starts to direct air (or other air) to the chamber 108 in step 1110. Pressure from the blower 110 forces air out the apertures 109 in the chamber 108. As the person 102 lies on the bed, the person's feet 103 protrude and create a space between the blanket 106 and bed 104. Air emerging from the nearby apertures 109 warms this space between the blanket 106 and bed 104, thereby surrounding the feet with warm air.

After steps 1108, 1110 start air flow and temperature regulation, step 1112 determines whether an operator has issued an "off" command, such as by turning off the regulator 113, blower 110, or a master control. If not, air flow and temperature regulation continue in step 1114. Otherwise, when the "off" command is detected, the routine 1100 ends in step 1116.

OTHER EMBODIMENTS

While the foregoing disclosure shows a number of illustrative embodiments of the invention, it wwill be apparent to those in the art that various changes and modifications can be made herein without departing from the scope of the invention as defined by the appended claims. Furthermore, although elements of the invention may be described or claimed in the singular, the plural is contemplated unless limitation to the singular is explicitly stated.

What is claimed is:

1. An apparatus to manage the temperature of air in a bed by directing air over the bed, comprising:
   an air permeable distribution chamber;
   a temperature regulating blower coupled to the chamber for providing pressurized warmed air to the chamber;
   a mattress having a sleeping surface and two opposing ends; and,
   a channel defined in the mattress on the top of the sleeping surface proximate one end of the mattress;
   the chamber residing in the channel for directing air at a normothermic temperature from the chamber, over the bed.

2. The apparatus of claim 1, the chamber comprising a length of open cell foam.

3. The apparatus of claim 1, the chamber comprising a substantially hollow conduit having a plurality of apertures defined therein.

4. The apparatus of claim 1, the chamber being substantially rigid.

5. The apparatus of claim 1, the chamber comprising a semi rigid, plastic material.

6. The apparatus of claim 1, the temperature regulating blower comprising:
   one or more heating elements; and,
   a temperature regulator varying heating intensity of the elements in unison.

7. The apparatus of claim 1, the temperature regulating blower comprising:
   multiple heating elements; and,
   a temperature regulator selectively activating individual ones of the heating elements to achieve a desired heating intensity.

8. The apparatus of claim 1, where the temperature regulating blower supplies air to the chamber at a temperature less than 40° Celsius.

9. The apparatus of claim 1, where the temperature regulating blower supplies air to the chamber at a temperature of approximately 38° Celsius.

10. The apparatus of claim 1, where the temperature regulating blower supplies air to the chamber at a hyperthermic temperature.

11. The apparatus of claim 1, where the bed has upper and lower layers of bedding and the chamber is positioned between the layers.

* * * * *

UNITED STATES PATENT AND TRADEMARK OFFICE
CERTIFICATE OF CORRECTION

PATENT NO. : 7,120,951 B2
APPLICATION NO. : 10/198842
DATED : October 17, 2006
INVENTOR(S) : Scott D. Augustine et al.

It is certified that error appears in the above-identified patent and that said Letters Patent is hereby corrected as shown below:

<u>Title Page, Page 2</u>
Under the heading OTHER PUBLICATIONS, replace "International Search Report for PCT/US00/41822." with --International Search Report for PCT/US00/41882.--

<u>Column 3</u>
Line 5, delete the word "hypothernic" and replace it with --hypothermic--.

Line 41, delete the word "a" in front of the word "adjustable" and replace it with --an--.

<u>Column 8</u>
Line 61, delete the word "wwill" and replace it with the word --will--.

Line 62, insert the word --skilled-- before the words "in the art".

Signed and Sealed this

First Day of July, 2008

JON W. DUDAS
*Director of the United States Patent and Trademark Office*